United States Patent
Breuil et al.

(10) Patent No.: US 10,421,066 B2
(45) Date of Patent: *Sep. 24, 2019

(54) NICKEL-BASED CATALYTIC COMPOSITION AND USE THEREOF IN A METHOD FOR THE OLIGOMERISATION OF OLEFINS

(71) Applicants: IFP Energies nouvelles, Rueil-Malmaison (FR); Universiteit Van Amsterdam, Pays-Bas (NL)

(72) Inventors: Pierre-Alain Breuil, Lyons (FR); Pierre Boulens, Lyons (FR); Joost Reek, Amersfoort (NL); Helene Olivier-Bourbigou, Saint Genis-Laval (FR)

(73) Assignees: IFP Energies Nouvelles, Rueil-Malmaison (FR); Universiteit Van Amsterdam, Amsterdam Pays Bas (NL)

( * ) Notice: Subject to any disclaimer, the term of this patent is extended or adjusted under 35 U.S.C. 154(b) by 590 days.

This patent is subject to a terminal disclaimer.

(21) Appl. No.: 14/901,495

(22) PCT Filed: Jun. 26, 2014

(86) PCT No.: PCT/FR2014/051626
§ 371 (c)(1),
(2) Date: Dec. 28, 2015

(87) PCT Pub. No.: WO2014/207394
PCT Pub. Date: Dec. 31, 2014

(65) Prior Publication Data
US 2016/0367978 A1    Dec. 22, 2016

(30) Foreign Application Priority Data

Jun. 28, 2013  (FR) ..................... 13 56269
Dec. 6, 2013   (FR) ..................... 13 62239

(51) Int. Cl.
| | |
|---|---|
| *B01J 31/24* | (2006.01) |
| *B01J 31/02* | (2006.01) |
| *B01J 31/18* | (2006.01) |
| *B01J 31/14* | (2006.01) |
| *C07C 2/36* | (2006.01) |

(52) U.S. Cl.
CPC ....... *B01J 31/2404* (2013.01); *B01J 31/0265* (2013.01); *B01J 31/143* (2013.01); *B01J 31/188* (2013.01); *B01J 31/189* (2013.01); *C07C 2/36* (2013.01); *B01J 2231/20* (2013.01); *B01J 2531/847* (2013.01); *C07C 2531/14* (2013.01); *C07C 2531/24* (2013.01)

(58) Field of Classification Search
None
See application file for complete search history.

(56) References Cited

U.S. PATENT DOCUMENTS

| | | | |
|---|---|---|---|
| 2005/0131262 A1* | 6/2005 | Dixon ................. | B01J 31/1805 585/511 |
| 2009/0069517 A1* | 3/2009 | De Boer ............. | B01J 31/0265 526/145 |
| 2011/0086991 A1* | 4/2011 | Dixon ...................... | B01J 31/18 526/139 |
| 2012/0178889 A1 | 7/2012 | De Boer et al. | |

OTHER PUBLICATIONS

Anagho et al., "Synthesis and Solid-State Structure of a Metal Complex of a Diphosphineimine", Angew. Chem. Int. Ed., 2005, 44, 3271-3275.*
International Search Report for PCT/FR2014/051626 dated Oct. 14, 2014.
Anagho, L. E. et al., "Synthesis and Solid-State Structure of a Metal Complex of a Diphosphineimine," Angewandte Chemie International Edition, Apr. 21, 2005, vol. 44, pp. 3271-3275.
Song, K. et al., "Syntheses, Structures, and Catalytic Ethylene Oligomerization Behavoirs of Bis(phosphanyl) aminenickel (II) Complexes containing N-functionalized Pendant Groups," European Journal of Inorganic Chemistry, Jul. 5, 2009, vol. 2009, No. 20, pp. 3016-3024.
Fei, Z. et al., "Understanding Structure Does Not Always Explain Reactivity: A phosphinoamide Anion Reacts as a Iminophosphide Anion," Inorganic Chemistry, American Chemical Society, Mar. 24, 2003, vol. 42, No. 6, pp. 2125-2130.
Zhaofu, F. et al., "Influence of the functional group on the synthesis of aminophosphines, diphosphinoamines and minobiphosphines," Jun. 6, 2003, vol. 2003, pp. 2772-2779.

* cited by examiner

*Primary Examiner* — In Suk C Bullock
*Assistant Examiner* — Ali Z Fadhel
(74) *Attorney, Agent, or Firm* — Millen, White, Zelano and Branigan, P.C.

(57) ABSTRACT

The invention describes a novel catalytic composition comprising at least one nickel precursor A with at least one diphosphinamine ligand B1 of formula (R1)(R'1)P—N(R3)—P(R2)(R'2) or an iminobisphosphine ligand B2 of formula (R3)N=P(R1)(R'1)—P(R2)(R'2) or an iminobisphosphine ligand B'2 of formula (R3)N=P(R2)(R'2)—P(R1)(R'1). The invention also describes the use of said catalytic composition in a method for the oligomerisation of olefins.

13 Claims, No Drawings

NICKEL-BASED CATALYTIC COMPOSITION AND USE THEREOF IN A METHOD FOR THE OLIGOMERISATION OF OLEFINS

The invention relates to a novel nickel-based catalytic composition. The invention also relates to the use of said catalytic composition as a catalyst in chemical transformation reactions.

PRIOR ART

It is known that nickel-based catalytic compositions can be prepared for application in various areas of chemistry, particularly in the area of catalytic transformations such as hydroformylation, hydrogenation, cross coupling, oligomerisation of olefins, etc.

Examples include the article *C.R. Acad. Sci.* 1967, C103-106 and the article *J. Mol. Catal.* A 2001, 169, 19-25 which describe nickel complexes in the presence of monophosphine.

The nickel diphosphinamine complexes described in the prior art are symmetric and prepared using diphosphinamine ligands in which the two phosphorous atoms are carriers of identical aromatic-type groups (*Eur. J. Inorg. Chem.*, 2009, 3016-3024, *Organometallics*, 2001, 20, 4769-4771). For example, patent application WO01/10876 describes nickel diphosphinamine complexes, with the symmetric ligands described being substituted, on the phosphorous, solely by aromatic groups, and used for the polymerisation of ethylene.

These catalytic systems are relatively inactive in the oligomerisation of ethylene and are generally used for the polymerisation of ethylene.

The applicant has discovered a novel nickel-based catalytic composition, prepared from dissymmetric diphosphinamine or iminobisphosphines ligands, in which one of the phosphorous atoms carries at least one non-aromatic group and the other phosphorous atom carries at least one aromatic group. It has been discovered that the compositions, whether or not a solvent is present, exhibit improved activity and selectivity for catalytic transformation reactions, in particular for the catalysis of olefin oligomerisation or dimerisation reactions.

DETAILED DESCRIPTION OF THE INVENTION

Catalytic Composition

A first object of the invention relates to a novel catalytic composition comprising:
- at least one nickel precursor A, with
- at least one diphosphinamine ligand B1 of formula $(R^1)(R'^1)P—N(R^3)—P(R^2)(R'^2)$,
- or an iminobisphosphine ligand B2 of formula $(R^3)N=P(R^1)(R'^1)—P(R^2)(R'^2)$,
- or an iminobisphosphine ligand B'2 of formula $(R^3)N=P(R^2)(R'^2)—P(R^1)(R'^1)$, in which
  - the groups $R^1$ and $R'^1$, which may be identical or different, and may or may not be linked, are selected from the non-aromatic groups,
  - the groups $R^2$ and $R'^2$, which may be identical or different, and may or may not be linked, are selected from the aromatic groups,
  - $R^3$ is selected from hydrogen, the halogens, the aliphatic hydrocarbon groups, cyclical or not, and which may or may not contain heteroelements, and the aromatic groups which may or may not contain heteroelements, which may or may not be substituted.

The groups $R^1$ and $R'^1$ are preferably selected from the non-aromatic groups not containing silicon. $R^1$ and $R'^1$ are preferably identical.

The groups $R^1$ and $R'^1$ are preferably selected from methyl, ethyl, isopropyl, n-butyl, iso-butyl, tert-butyl, pentyl and cyclohexyl groups, which may or may not be substituted.

The groups $R^2$ and $R'^2$ are preferably selected from phenyl, o-tolyl, m-tolyl, p-tolyl, mesityl, 3,5-dimethylphenyl, 4-methoxyphenyl, 2-methoxyphenyl, 2-isopropoxyphenyl, 4-methoxy-3,5-dimethylphenyl, 3,5-di-tert-butyl-4-methoxyphenyl, 3,5-bis(trifluoromethyl)phenyl, benzyl, naphthyl and pyridyl groups, which may or may not be substituted, which may or may not contain heteroelements. $R^2$ and $R'^2$ are preferably identical.

Advantageously, $R^3$ is selected from hydrogen, the alkoxy, aryloxy, sulphur, sulfonamine, sulfonamide, nitro, carbonyl, amino and amido groups which may or may not comprise aliphatic, cyclical or aromatic groups, which may or may not contain heteroelements, which may or may not be substituted.

The nickel precursor A can be selected from nickel (II) chloride, nickel(II)(dimethoxyethane) chloride, nickel(II) bromide, nickel(II)(dimethoxyethane) bromide, nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates such as 2-ethylhexanoate, for example, nickel (II) phenates, nickel(II) acetate, nickel(II) trifluoroacetate, nickel(II) triflate, nickel(II) acetylacetonate, nickel(II) hexafluoroacetylacetonate, nickel(0) bis(cycloocta-1,5-diene), nickel(0) bis(cycloocta-1,3-diene), nickel(0) bis(cyclooctatetraene), nickel(0) bis(cycloocta-1,3,7-triene), bis (o-tolylphosphito) nickel(0)(ethylene), nickel(0) tetrakis (triphenylphosphite), nickel(0) tetrakis(triphenylphosphine), nickel(0) bis(ethylene), π-allylnickel(II) chloride, π-allylnickel(II) bromide, methallylnickel(II) chloride dimer, $\eta^3$-allylnickel(II) hexafluorophosphate, $\eta^3$-methallylnickel (II) hexafluorophosphate, and nickel(II) (1,5-cyclooctadiene) in their hydrated or non-hydrated form, used alone or as a mixture. Said nickel precursors may optionally be complexed with Lewis bases.

Preparation of the diphosphinamine ligands B1 of formula (R1)(R'1)P—N(R3)-P(R2)(R'2), or iminobisphosphine ligands B2 of formula (R3)N=P(R1)(R'1)-P(R2)(R'2) or iminobisphosphine ligands B'2 of formula (R3)N=P(R2)(R'2)-P(R1)(R'1), takes place according to methods known from the literature (Inorg. Chem. 2003, 2125-2130). The diphosphinamine ligands B1 of formula (R1)(R'1)P—N (R3)-P(R2)(R'2) can be prepared and isolated by reacting 1 equivalent of chlorophosphine Cl—P(R1)(R'1) and 1 equivalent of chlorophosphine Cl—P(R2)(R'2) with a primary or aromatic amine R3-NH2 in the presence of triethylamine. The iminobisphosphine ligands B2 of formula (R3)N=P(R1)(R'1)-P(R2)(R'2) can be prepared and isolated by reacting a primary or aromatic amine R3-NH$_2$ and 1 equivalent of chlorophosphine Cl—P(R1)(R'1) and 1 equivalent of chlorophosphine Cl—P(R2)(R'2) introduced one after the other in the presence of triethylamine. The iminobisphosphine ligands B'2 of formula (R3)N=P(R2) (R'2)-P(R1)(R'1) can be prepared and isolated by reacting a primary or aromatic amine R3-NH$_2$ and 1 equivalent of chlorophosphine Cl—P(R2)(R'2) and 1 equivalent of chlorophosphine Cl—P(R1)(R'1) introduced one after the other in the presence of triethylamine.

Use of the Catalytic Composition in a Chemical Transformation Reaction

The catalytic composition according to the invention can be used in a chemical transformation reaction, such as a reaction for hydrogenation, hydroformylation, cross coupling or oligomerisation of olefins. In particular, the catalytic composition according to the invention is used in a process for oligomerisation of olefins advantageously comprising between 2 and 10 carbon atoms; preferably in a process of dimerisation of ethylene or propylene.

The catalytic composition according to the invention can be used in a mixture with a compound C known as an activating agent. Said activating agent is advantageously selected from the group formed by tris(hydrocarbyl)aluminium compounds, chlorine-containing or bromine-containing hydrocarbylaluminium compounds, aluminium halides, aluminoxanes, organo-boron compounds, and organic compounds which are susceptible of donating or accepting a proton, used alone or as a mixture.

The tris(hydrocarbyl)aluminium compounds, the chloride-containing and bromine-containing hydrocarbylaluminium compounds and the aluminium halides preferably adhere to the general formula $Al_xR_yW_z$ in which R represents a monovalent hydrocarbon radical containing for example up to 12 carbon atoms such as alkyl, aryl, aralkyl, alkaryl or cycloalkyl, W represents a halogen atom selected for example from chlorine and bromine, W preferably being a chlorine atom, x takes a value of between 1 and 2, and y and z take a value of between 0 and 3. Examples of compounds of this type which may be mentioned are ethylaluminium sesquichloride ($Et_3Al_2Cl_3$), methylaluminium dichloride ($MeAlCl_2$), ethylaluminium dichloride ($EtAlCl_2$), isobutylaluminium dichloride ($iBuAlCl_2$), diethylaluminium chloride ($Et_2AlCl$), trimethylaluminium, tributylaluminium, tri-n-octylaluminium and triethylaluminium ($AlEt_3$).

In the case in which said activating agent is selected from aluminoxanes, said activating agent is advantageously selected from methylaluminoxane (MAO), ethylaluminoxane and modified methylaluminoxanes (MMAO). These activating agents may be used alone or as a mixture.

Preferably, said activating agent C is selected from dichloroethylaluminium ($EtAlCl_2$) and methylaluminoxane (MAO).

In the case in which said activating agent is selected from organo-boron compounds, said activating agent is preferably selected from Lewis acids of the tris(aryl)borane type, such as tris(perfluorophenyl)borane, tris(3,5-bis(trifluoromethyl) phenyl)borane, tris(2,3,4,6-tetrafluorophenyl)borane, tris (perfluoronaphtyl)borane, tris(perfluorobiphenyl)borane and their derivatives and (aryl)borates associated with a triphenylcarbenium cation, or a trisubstituted ammonium cation such as triphenylcarbenium tetrakis(perfluorophenyl)borate, N,N-dimethylanilinium tetrakis(perfluorophenyl)borate, N,N-diethylanilinium tetrakis(3,5-bis(trifluoromethyl)phenyl)borate, or triphenylcarbenium tetrakis(3,5-bis(trifluoromethyl)phenyl)borate.

In the case in which said activating agent is selected from organic compounds which are susceptible of donating a proton, said activating agent is preferably selected from acids with formula HY in which Y represents an anion.

In the case in which said activating agent is selected from organic compounds which are susceptible of accepting a proton, said activating agent is preferably selected from Brönsted bases.

The catalytic composition according to the invention is advantageously used in a process of oligomerisation or dimerisation of olefins, preferably in a process of dimerisation of ethylene or propylene.

The solvent for the oligomerisation or dimerisation process may be selected from organic solvents, preferably from ethers, alcohols, chlorine-containing solvents and saturated, unsaturated, aromatic or non-aromatic, cyclic or non-cyclic hydrocarbons. In particular, said solvent is selected from hexane, cyclohexane, methylcyclohexane, heptane, butane or isobutane, monoolefins or diolefins preferably containing 4 to 20 carbon atoms, benzene, toluene, ortho-xylene, mesitylene, ethylbenzene, dichloromethane, chlorobenzene, methanol and ethanol, pure or as a mixture, and ionic liquids. In the case in which said reaction solvent is an ionic liquid, it is advantageously selected from the ionic liquids described in patents U.S. Pat. No. 6,951,831 B2 and FR 2 895 406 B1.

The catalytic compositions according to the invention may be prepared in situ in the reaction section or elsewhere.

Oligomerisation is defined as the transformation of a monomer unit into a compound or mixture of compounds with general formula $C_pH_{2p}$, with $4 \leq p \leq 80$, preferably with $4 \leq p \leq 50$, more preferably with $4 \leq p \leq 26$ and highly preferably with $4 \leq p \leq 14$.

The olefins used in the oligomerisation or dimerisation process are olefins containing 2 to 10 carbon atoms. Preferably, said olefins are selected from ethylene, propylene, n-butenes and n-pentenes, alone or as a mixture, pure or diluted.

In the case in which said olefins are diluted, said olefins are diluted with one or more alkane(s) such as those found in "cuts" obtained from oil refining processes such as catalytic cracking or steam cracking.

Preferably, the olefin used in the oligomerisation or dimerisation process is ethylene or propylene.

Said olefins may be obtained from non-fossil sources such as biomass. As an example, the olefins used in the oligomerisation process according to the invention may be produced from alcohols, in particular by dehydration of alcohols.

The concentration of nickel in the catalytic solution is advantageously in the range $1 \times 10^{-8}$ to 1 mol/l, and preferably in the range $1 \times 10^{-6}$ to $1 \times 10^{-2}$ mol/l.

The molar ratio between the ligand B1 or B2 or B'2 and the nickel precursor A is advantageously between 0.05 and 10, preferably between 0.5 and 2 and more preferably 1.

The molar ratio between the activating agent C and the nickel precursor is advantageously between 1/1 and 10,000/1, preferably between 1/1 and 1,000/1 for the aluminoxanes and preferably between 1/1 and 100/1 for the other aluminium derivatives and the other Lewis acids.

The oligomerisation and dimerisation method according to the invention is advantageously operated at a total pressure in the range between atmospheric pressure and 20 MPa, preferably in the range 0.5 to 8 MPa, and at a temperature in the range −40° C. to +250° C., preferably in the range −20° C. to 150° C.

The following examples illustrate the invention without limiting its scope. The notation "Cy" represents the tricyclohexyl group.

EXAMPLE 1

Synthesis of Ligands

Iminobisphosphine ligands R'—$SO_2$—N=P($R^1$)($R'^1$)—P($R^2$)($R'^2$) were prepared and isolated by reacting a sulfonamide and 2 equivalents of chlorophosphine (which may be identical or different) in the presence of triethylamine. Examples are provided by ligands 1 and 2 in which $R^1=R'^1=R^2=R'^2$ (comparative examples) and ligands 3, 3', 4 and 4' in which $R^1=R'^1$ and $R^2=R'^2$ and $R^1$ is different from $R^2$. The structures of the four ligands are shown below.

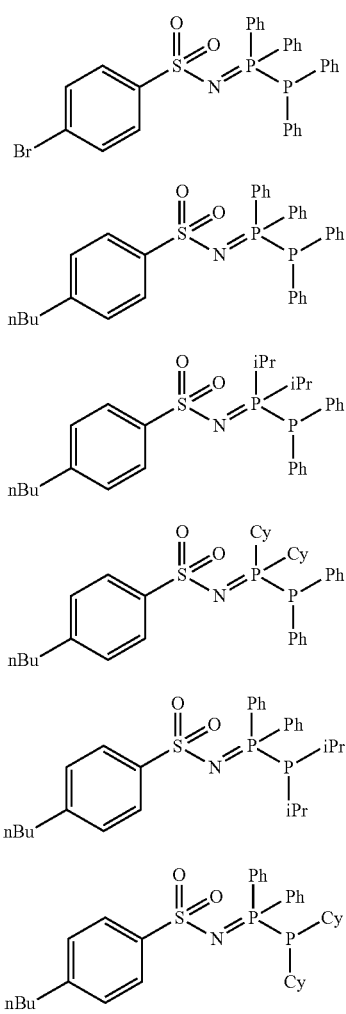

Synthesis of Ligand 1:
4-bromo-N-(1,1,2,2-tetraphenyldiphosphanylidene) benzenesulfonamide Freshly distilled chlorodiphenylphosphine (0.760 ml, 4.24 mmol, 2 eq.) was added drop by drop to a solution of 4-bromobenzenesulfonamide (500 mg, 2.12 mmol, 1 eq.) and triethylamine (1.6 ml, 11.2 mmol, 5.3 eq.) in THF (10 ml) at ambient temperature and under vigorous agitation. Once addition was complete, the mixture was agitated for 5 minutes and then the suspension was filtered under a nitrogen atmosphere on a sintered glass filter. Evaporation of the solvent and the volatile components led to the formation of a solid. This solid was dissolved in a minimum of dichloromethane, then pentane (20 ml) was added. By evaporating this solution, a precipitate appeared. The supernatant was removed using a syringe and the solid was then washed with pentane (2×10 ml) and dried under a vacuum to provide ligand 1 in the form of a white powder (isolated yield: 68%).

$^1$H NMR (300 MHz, $CD_2Cl_2$): δ 7.82-6.89 (m, 24H). $^{31}$P NMR (121 MHz, $CD_2Cl_2$) 19.72 (d, J=281.1 Hz), −18.74 (d, J=281.1 Hz).

$^{31}$P{$^1$H} NMR (121 MHz, $CD_2Cl_2$): 19.72 (d, J=279.9 Hz), −18.74 (d, J=281.2 Hz).

MS (FAB$^+$): m/z calc. for $C_{30}H_{25}NO_2P_2BrS$ ([MH]$^+$): 606.0248; obs.: 606.0255.

Synthesis of Ligand 2:
4-butyl-N-(1,1,2,2-tetraphenyldiphosphanylidene) benzenesulfonamide Freshly distilled chlorodiphenylphosphine (0.840 ml, 4.68 mmol, 2 eq.) was added drop by drop to a solution of 4-butylbenzenesulfonamide (500 mg, 2.34 mmol, 1 eq.) and triethylamine (1 ml, 7.17 mmol, 3 eq.) in THF (20 ml), at ambient temperature and under vigorous agitation. Once addition was complete, the mixture was agitated for 5 minutes and then the suspension was filtered under a nitrogen atmosphere on a sintered glass filter. Evaporation of the solvent and the volatile components led to the formation of an oil. This oil was solubilised in diethyl ether (10 ml) and the solution evaporated. This step was repeated 4 times until the product precipitated. The solid was then dried under a vacuum to provide ligand 2 in the form of a white powder (isolated yield: 79%).

$^1$H NMR (300 MHz, $CD_2Cl_2$): δ 7.91-6.33 (m, —$CH_{Ar}$, 24H), 2.59 (t, $CH_3$—$CH_2$—$CH_2$—$\underline{CH_2}$—CAr, J=7.7 Hz, 2H), 1.57 (m, $CH_3$—$CH_2$—$\underline{CH_2}$—$CH_2$—CAr, 2H), 1.33 (m, $CH_3$—$\underline{CH_2}$—$CH_2$—$CH_2$—Car, 2H), 0.93 (t, $\underline{CH_3}$—$CH_2$—$CH_2$—$CH_2$—Car, J=7.3 Hz, 3H).

$^{31}$P NMR (121 MHz, $CD_2Cl_2$): δ 19.47 (d, J=277.9 Hz), −17.90 (d, J=278.0 Hz).

MS (FAB+): m/z calc. for $C_{34}H_{34}O_2NP_2S$ ([M+H]$^+$): 582.1786; obs.: 582.1790

Synthesis of N-diphenylphosphino-4-butylbenzenesulfonamide

Freshly distilled chlorodiphenylphosphine (9.38 mmol, 1 eq.) was added drop by drop to a solution of 4-butylbenzene-1-sulfonamide (9.38 mmol, 1 eq.) and triethylamine (25 mmol) in THF (20 ml), at ambient temperature and under vigorous agitation. The suspension was left under agitation for one night at ambient temperature. Evaporation of the solvent and the volatile components led to the formation of a solid. This solid was dissolved in 10 ml of dichloromethane, and then pentane (40 ml) was added, with the appearance of a precipitate. The supernatant was removed using a syringe and the solid was then washed with pentane (2×20 ml) and dried under a vacuum to provide N-diphenylphosphino-4-butylbenzenesulfonamide in the form of a white powder. This compound could be isolated and purified or used directly in another stage of synthesis (isolated yield: 74%).

Synthesis of Ligand 3: 4-butyl-N-(1,1-diisopropyl-2,2-diphenyldiphosphanylidene) benzenesulfonamide Diisopropylchlorophosphine (0.746 ml, 4.68 mmol, 1 eq.) was added drop by drop to a solution of N-diphenylphosphino-4-butylbenzenesulfonamide (1.86 g, 4.68 mmol, 1 eq.) and triethylamine (1.30 ml, 9.36 mmol, 2 eq.) in THF (20 ml), at ambient temperature and under vigorous agitation. Once addition was complete, the mixture was agitated for 10 minutes and then the suspension was filtered under a nitrogen atmosphere on a sintered glass filter. Evaporation of the solvent and the volatile components led to the formation of an oil. Pentane (20 ml) was added to this oil, then following trituration the pentane was removed using a syringe. The oil was then suspended in pentane (10 ml) and the solution evaporated under a vacuum. This step was repeated once with pentane and then twice with diethyl ether (10 ml) allowing the formation of a solid. The solid was washed with pentane (2×10 ml) then dried under a vacuum to provide ligand 3 in the form of a white solid (isolated yield: 34%).

$^1$H (300 MHz, $CD_2Cl_2$): δ: δ 7.98-7.83 (m, 4H, —P<u>Ph</u>$_2$), 7.76-7.64 (m, 2H,—$CH_2$—<u>Ar</u>—$SO_2$), 7.60-7.35 (m, 6H, —P<u>Ph</u>$_2$), 7.23-7.12 (m, 2H, —$CH_2$—<u>Ar</u>—$SO_2$), 2.69-2.57 (t, 2H, J=7.4 Hz, $CH_3$—$CH_2$—$CH_2$—<u>$CH_2$</u>—Ar), 2.44 (m, 2H, $CH_3$—<u>CH</u>—$CH_3$), 1.69-1.48 (m, 2H, $CH_3$—$CH_2$—<u>$CH_2$</u>—$CH_2$—Ar), 1.35 (m, 2H, $CH_3$—<u>$CH_2$</u>—$CH_2$—$CH_2$—Ar), 1.18-0.99 (m, 12H, <u>$CH_3$</u>—CH—<u>$CH_3$</u>), 0.93 (t, J=7.3 Hz, 3H, <u>$CH_3$</u>—$CH_2$—$CH_2$—$CH_2$—Ar).

$^{31}$P(121 MHz, $CD_2Cl_2$) δ: 20.13 (d, J=311.6 Hz); 2.80 (d, J=311.6 Hz).

Synthesis of Ligand 4: 4-butyl-N-(1,1-dicyclohexyl-2,2-diphenyldiphosphanylidene) benzenesulfonamide Dicyclohexylylphosphine (0.200 ml, 0.91 mmol, 1 eq.) was added drop by drop to a solution of N-diphenylphosphino-4-butylbenzenesulfonamide (0.361 g, 0.91 mmol, 1 eq.) and triethylamine (0.126 ml, 1.82 mmol, 2 eq.) in THF (10 ml), at ambient temperature and under vigorous agitation. Once addition was complete, the mixture was agitated for 5 minutes and then the suspension was filtered under a nitrogen atmosphere on a sintered glass filter. Evaporation of the solvent and the volatile components led to the formation of an oil. Pentane (10 ml) was added to this oil, then following trituration it was evaporated under a vacuum. This step was repeated once with pentane and then twice with diethyl ether (10 ml) allowing the formation of a solid. The solid was dried under a vacuum to provide ligand 4 in the form of a white solid (isolated yield: 51%).

$^1$H NMR (300 MHz, $CD_2Cl_2$): δ 7.90 (dd, J=12.5, 7.6 Hz, 4H, P<u>Ph</u>$_2$), 7.78-7.67 (dd, J=8.4, 2.0 Hz, 2H, <u>Ar</u>—$SO_2$), 7.61-7.40 (m, 6H, P<u>Ph</u>$_2$), 7.18 (dd, J=8.4, 2.0 Hz, 2H, <u>Ar</u>—$SO_2$), 2.63 (t, J=7.6 Hz, 2H, —<u>$CH_2$</u>—Ar), 2.30-2.01 (m, 2H, <u>Cy</u>), 1.81 (m, 2H, <u>Cy</u>), 1.73-1.49 (m, 8H, <u>Cy</u>), 1.73-1.49 (m, 2H, —<u>$CH_2$</u>—$CH_2$—Ar) 1.33 (dt, J=16.3, 7.3 Hz, 2H, —<u>$CH_2$</u>—$CH_2$—$CH_2$—Ar), 1.17 (m, 10H, Cy), 0.93 (t, J=7.3 Hz, 3H, <u>$H_3C$</u>—$CH_2$—$CH_2$).

$^{31}$P NMR (121 MHz, $CD_2Cl_2$): δ 20.44 (d, J=314.9 Hz), -4.98 (d, J=314.4 Hz).

MS (FAB+): m/z calcd. For $C_{34}H_{34}O_2NP_2S$ ([M+H]$^+$): 594.2725; obsd.: 594.2732.

Preparation of the Compositions

Ligands 1, 2, 3, 3', 4 and 4' were placed in a mixture with $NiBr_2$(dme) to provide the compositions 5, 6, 7, 7', 8 and 8' respectively. Composition 9 is a reference composition comprising tricyclohexylphosphine and $NiCl_2$.

Preparation of Composition 5 (Comparative)
4-bromo-N-(1,1,2,2-tetraphenyldiphosphanylidene)benzenesulfonamide 1 (200 mg, 0.331 mmol, 1.01 eq.) and nickel(II)(dimethoxyethane) bromide (101 mg, 0.327 mmol, 1 eq.) were suspended in toluene (3 ml). The solution was then evaporated and diluted in the reaction solvent.

Preparation of Composition 6 (Comparative)
4-butyl-N-(1,1,2,2-tetraphenyldiphosphanylidene)benzenesulfonamide 2 (200 mg, 0.344 mmol, 1 eq.) and nickel (II)(dimethoxyethane) bromide (106 mg, 0.344 mmol, 1 eq.) were suspended in toluene (3 ml).

Preparation of Composition 7
4-butyl-N-(1,1-diisopropyl-2,2-diphenyldiphosphanylidene)benzenesulfonamide 3 (400 mg, 0.786 mmol, 1 eq.) and nickel(II)(dimethoxyethane) bromide (266 mg, 0.864 mmol, 1.1 eq.) were suspended in dichloromethane (5 ml).

Preparation of Composition 7'
4-butyl-N-(1,1-diphenyl-2,2-diisopropyldiphosphanylidene)benzenesulfonamide 3' (400 mg, 0.786 mmol, 1 eq.) and nickel(II)(dimethoxyethane) bromide (266 mg, 0.864 mmol, 1.1 eq.) were suspended in dichloromethane (5 ml).

Preparation of Composition 8
4-butyl-N-(1,1-dicyclohexyl-2,2-diphenyldiphosphanylidene)benzenesulfonamide 4 (98 mg, 0.165 mmol, 1.02 eq.) and nickel(II)(dimethoxyethane) bromide (50 mg, 0.162 mmol, 1 eq.) were suspended in dichloromethane (3 ml).

Preparation of Composition 8'
4-butyl-N-(1,1-diphenyl-2,2-dicyclohexyl diphosphanylidene)benzenesulfonamide 4' (98 mg, 0.165 mmol, 1.02 eq.) and nickel(II)(dimethoxyethane) bromide (50 mg, 0.162 mmol, 1 eq.) were suspended in dichloromethane (3 ml).

EXAMPLE 2

Oligomerisation of Ethylene

The ethylene oligomerisation reaction was evaluated with compositions 5 and 6 and 7, 7' and 8' in the presence of methylaluminoxane (MAO) at 45° C. and under 30 bar of ethylene (1 bar=0.1 MPa).

Operating conditions: The 100 ml reactor was dried under a vacuum at 100° C. for 2 hours and pressurised with ethylene. The catalyst was introduced (0.1 mmol in 8 ml of toluene) followed by methylaluminoxane (2 ml, 10% in toluene, 300 eq.). The temperature and the pressure were set at 45° C. and 35 bar. Agitation was commenced (t=0). After the set reaction time, the reactor was cooled to ambient temperature and depressurised under agitation. The liquid phase was neutralised with aqueous $H_2SO_4$ and analysed by GC.

Compositions 5 and 6 activated by MAO (300 eq.) were considered to be inactive, as the consumption of ethylene was negligible. Compositions 7, 7' and 8' activated by MAO were highly active during oligomerisation of ethylene (activity greater than $4·10^6$ $g_{C_2H_4}/(mol_{Ni}·h)$) and no polymer was formed. The GC analyses confirmed that the products formed were principally butenes and hexenes. The results are shown in Table 1.

TABLE 1

Oligomerisation of ethylene catalysed by 5, 6, 7, 7' and 8'.[a]

| Entry | Composition | Time (min.) | Cons. $C_2H_4$ (g) | Activity[b] | Distribution by oligomers [wt. %] | | | | |
|---|---|---|---|---|---|---|---|---|---|
| | | | | | $C4^c$ | $C6^c$ | $C8^{+c}$ | $1-C4^d$ | $2-C4^d$ |
| 1[e] | 5 | 22 | N.d.[f] | — | — | — | — | — | — |
| 2[e] | 6 | 20 | N.d.[f] | — | — | — | — | — | — |
| 3 | 7 | 14 | 31.5 | 14 · 10$^6$ | 60.3 | 25.7 | 14.0 | 6.6 | 93.4 |

TABLE 1-continued

Oligomerisation of ethylene catalysed by 5, 6, 7, 7' and 8'.[a]

| Entry | Composition | Time (min.) | Cons. $C_2H_4$ (g) | Activity[b] | Distribution by oligomers [wt. %] | | | | |
|---|---|---|---|---|---|---|---|---|---|
| | | | | | C4[c] | C6[c] | C8+[c] | 1-C4[d] | 2-C4[d] |
| 4[g] | 7' | 45 | 36.2 | $4.8 \cdot 10^6$ | 71.7 | 17.9 | 10.4 | 20.9 | 79.1 |
| 5[g] | 8' | 48 | 32.7 | $4.1 \cdot 10^6$ | 69.2 | 19.7 | 11.1 | 22.2 | 77.8 |

[a]Reaction conditions: $n_{ni}$ = 10 μmol, co-catalyst: MAO (300 eq.), 30 bar $C_2H_4$, 45° C., solvent: toluene (10 ml).
[b]$g_{C2H4}/(mol_{Ni} \cdot h)$.
[c]Determined by GC, wt. %/all oligomers.
[d]wt. %/to the other products of cut C4.
[e]Comparative examples.
[f]Not determined: ethylene consumption negligible, activities observed < $10^6$.
[g]solvent: toluene (50 ml).

Composition 7 comprising the dissymmetric ligand 3 led to performances that were far superior in terms of activity to compositions 5 or 6 comprising symmetric ligands 1 and 2. Compositions 7' and 8' comprising dissymmetric ligands 3' and 4', respectively led to performances that were far superior in terms of activity to compositions 5 or 6 comprising symmetric ligands 1 and 2.

EXAMPLE 3

Oligomerisation of Propylene

The oligomerisation of propylene was performed with two different activating agents: EADC (ethylaluminium dichloride) and MAO (methylaluminoxane). The tests performed with composition 9 $NiCl_2(PCy_3)_2$ are reference tests.
Tests with EADC
Operating conditions: The 250 ml reactor was dried under a vacuum at 100° C. for 2 hours, cooled to 10° C. and then filled with propylene (pressure of 1.4 bar). 33 ml of chlorobenzene and 10 ml of n-heptane (accurately weighed internal standard) were then introduced, followed by 8 g of propylene. The reactor was cooled to −10° C. under agitation. The EADC (ethylaluminium dichloride, 0.075 M in toluene, 15 eq., 2 ml) activating agent was then injected, followed by the catalyst (0.1 mmol in 5 ml of chlorobenzene). 12 g of propylene were then introduced. Agitation was then commenced (t=0). The temperature was maintained at −10° C. for 10 minutes and then smoothly increased to 10° C. The consumption of propylene was followed by a reduction in pressure. The liquid phase was then removed and neutralised with aqueous NaOH. The organic phase was weighed and analysed by a GC fitted with a cryostat. The results are shown in Table 2.

Following activation with the EADC activating agent, compositions 7, 8 and 9 were highly active for the oligomerisation of propylene at 10° C. The C6 selectivity of compositions 7 and 8 was superior to reference composition 9. The 1-dimethylbutene and 2-dimethylbutene selectivity was approximately 25% for activated compositions 7 and 8.

TABLE 2

Oligomerisation of propylene with different compositions activated by the EADC activating agent.[a]

| Entry | Composition | Time (min.) | Activity[b] | Distribution by oligomers [wt. %][c] | | | |
|---|---|---|---|---|---|---|---|
| | | | | C6 | C9 | C12 | C15+ |
| 1[d] | 6 | 54 | Inactive | | | | |
| 2 | 7 | 30 | 4 | 96.8 | 2.9 | 0.2 | 0.1 |
| 3 | 8 | 5 | 24 | 97.1 | 2.3 | 0.2 | 0.4 |
| 4[d] | 9 | 42 | 2.9 | 86.4 | 12.1 | 1.3 | 0.2 |

[a]Reaction conditions: $n_{ni}$ = 10 μmol, co-catalyst: EADC (15 eq.), 20 g $C_3H_6$, 10° C., solvent: chlorobenzene (50 ml).
[b]$10^6 \ g_{oligo} \cdot mol_{Ni}^{-1} \cdot h^{-1}$.
[c]Determined by GC with n-heptane as internal standard.
[d]Comparative example.

The dimer selectivity obtained with compositions 7, 8 and 9 activated with the EADC activating agent is shown in Table 3.

TABLE 3 dimer selectivity

| Entry | Composition | 4M1P | 1-DMB | 4M2P | 2M1P | 2M2P | Hex | 2-DMB |
|---|---|---|---|---|---|---|---|---|
| 2 | 7 | 1.2 | 23.7 | 35.5 | 13 | 13.4 | 11.4 | 1.8 |
| 3 | 8 | 1.1 | 17.3 | 43.3 | 12.4 | 11 | 13.6 | 1.3 |
| 4[a] | 9 | 6.6 | 62.2 | 10.9 | 17.2 | 0.5 | 2.4 | 0.2 |

Dimer selectivity in wt. %, determined by GC. 4M1P: 4-methylpentene-1, 1-DMB: 2,3-dimethylbutene-1, 4M2P: 4-methylpentene-2, 2M1P: 2-methylpentene-1, 2M2P: 2-methylepentene-2, Hex: linear hexenes, 2-DMB: 2,3-dimethylbutene-2.
[a]Comparative examples.

The above examples show that the catalytic compositions used in the method according to the invention have an improved activity and selectivity for the oligomerisation of olefins comprising preferably between 2 and 10 carbon atoms, more specifically for the dimerisation of olefins comprising between 2 and 10 carbon atoms.

The invention claimed is:
1. A catalytic composition comprising:
   at least one nickel compound A, with a ligand that is
   at least one diphosphinamine ligand B1 of formula $(R^1)(R^{i1})P-N(R^3)-P(R^2)(R^{i2})$,
   or an iminobisphosphine ligand B2 of formula $(R^3)N=P(R^1)(R^{i1})-P(R^2)(R^{i2})$,
   or an iminobisphosphine ligand B'2 of formula $(R^3)N=P(R^2)(R^{i2})-P(R^1)(R^{i1})$, in which
   the groups $R^1$ and $R^{i1}$, which may be identical or different, and may or may not be linked, are a non-aromatic group not containing silicon, the groups $R^2$ and $R'^2$, which may be identical or different, and may or may not be linked, are an aromatic group, $R^3$ is sulfonamide.

2. The composition according to claim 1 in which the groups $R^1$ and $R'^1$ are substituted or unsubstituted methyl, ethyl, isopropyl, n-butyl, iso-butyl, tert-butyl, pentyl, or cyclohexyl groups.

3. The composition according to claim 1 in which the groups $R^2$ and $R'^2$ are phenyl, o-tolyl, m-tolyl, p-tolyl, mesityl, 3,5-dimethylphenyl, 4-methoxyphenyl, 2-methoxyphenyl, 2-isopropoxyphenyl, 4-methoxy-3,5-dimethylphenyl, 3,5-ditert-butyl-4-methoxyphenyl, 3,5-bis(trifluoromethyl)phenyl, benzyl, naphthyl or pyridyl, which is optionally substituted and optionally contains heteroelements.

4. The composition according to claim 1 furthermore comprising an activating agent C that is tris(hydrocarbyl) aluminium compound, chlorine-containing or bromine-containing hydrocarbylaluminium compound, aluminoxane, organo-boron compound, acids having formula HY wherein Y is an anion, or Brønsted base, used alone or as a mixture.

5. The composition according to claim 4, having a molar ratio of activating agent C to nickel compound of 1/1 to 10,000/1.

6. The composition according to claim 1, wherein the ligand is 3,3',4 or 4'

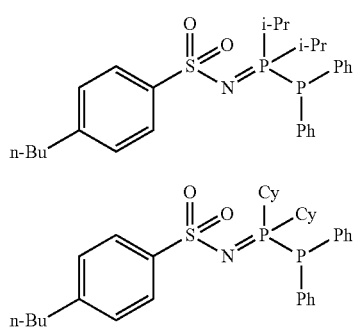

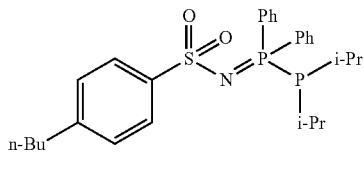

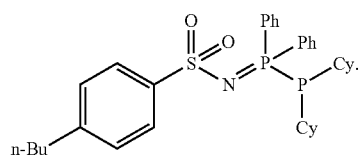

7. The composition according to claim 1, having a molar ratio of ligand to nickel compound of 0.05 to 10.

8. A method for oligomerisation of an olefins feed comprising bringing said feed into contact with the composition according to claim 1, optionally in the presence of a solvent.

9. The method according to claim 8 in which the olefins are ethylene, propylene, n-butenes or n-pentenes, alone or as a mixture, pure or diluted.

10. The method according to claim 8 in which the nickel compound is present in a concentration of $1\times10^{-8}$ to 1 mol/l.

11. The method according to claim 8 the oligomerisation is operated at a pressure of atmospheric pressure to 20 MPa, and at a temperature of −40° C. to +250° C.

12. The method according to claim 8 in which the oligomerisation is a dimerization.

13. The method according to claim 12 in which the oligomerisation is an ethylene or propylene dimerization.

* * * * *